United States Patent [19]

Laustsen

[11] Patent Number: 5,437,774
[45] Date of Patent: Aug. 1, 1995

[54] HIGH MOLECULAR WEIGHT ELECTRODIALYSIS

[75] Inventor: Mads Laustsen, Lynghy, Denmark

[73] Assignee: Zymogenetics, Inc., Seattle, Wash.

[21] Appl. No.: 176,037

[22] Filed: Dec. 30, 1993

[51] Int. Cl.$^6$ ............................................. B01D 61/42
[52] U.S. Cl. .............................. 204/182.3; 204/182.6; 204/183.1; 204/301
[58] Field of Search ................... 205/182.3, 182.6, 301, 205/183.2

[56] References Cited

U.S. PATENT DOCUMENTS

| | | | |
|---|---|---|---|
| 4,123,342 | 10/1978 | Ahlgren | 204/182.1 |
| 4,276,140 | 6/1981 | Jain | 204/180 |
| 4,332,275 | 6/1982 | Brown | 137/504 |
| 4,351,710 | 9/1982 | Jain | 204/180 |
| 4,362,612 | 12/1982 | Bier | 204/301 |
| 4,396,477 | 8/1983 | Jain | 204/180 |
| 4,441,978 | 4/1984 | Jain | 204/301 |
| 4,971,670 | 11/1990 | Faupel et al. | 204/182 |
| 5,082,548 | 1/1992 | Faupel et al. | 204/299 |
| 5,085,749 | 2/1992 | Grimshaw et al. | 204/182.1 |
| 5,223,107 | 6/1993 | Batchelder | 204/182 |

FOREIGN PATENT DOCUMENTS

| | | |
|---|---|---|
| 9112726 | 9/1991 | WIPO . |
| 9207818 | 5/1992 | WIPO . |

OTHER PUBLICATIONS

Kirk–Othmer, *Encyclopedia of Chemical Technology*, vol. 8, pp. 726–738, Wiley & Sons, New York, 1986.

Reed, P. (Oct. 1985) *Genetic Engineering News*, vol. 5, No. 9, p. 10 "Electrodialysis: Large Scale Processing of Protein Solutions".

Wenisch, E., et al. (1992) "Purification to Single Isoforms of a Secreted Epidermal Growth Factor Receptor in a Multi–compartment Electrolyzer with Isoelectric Membranes" *Electrophoresis* 13:668–673.

*Primary Examiner*—John Niebling
*Assistant Examiner*—Arun S. Phasge
*Attorney, Agent, or Firm*—Townsend and Townsend Khourie and Crew

[57] ABSTRACT

A charged first molecular species is separated from a second molecular species by selectively passing one of the species through a separation membrane under the influence of an electrical potential. The separated species is maintained within a dialysate stream by retention membrane (or an electrode surface) adjacent the separation membrane. In a first embodiment, the charged species migrates across the separation membrane under the influence of the electric field, while a neutral or oppositely-charged species is maintained within the aqueous media. In the second embodiment, the charged species is maintained with the load channel, while a neutral species is passed into the dialysate chamber under the influence of a differential pressure.

59 Claims, 9 Drawing Sheets

HIGH MOLECULAR WEIGHT ELECTRODIALYSIS

BACKGROUND OF THE INVENTION

1. Field of the Invention

The present invention relates generally to chemical separation processes and equipment, and more particularly to a method and apparatus for purifying proteins and other high molecular weight compounds from complex media, such as biological media.

The selective separation of high molecular weight compounds from one another is of importance to many chemical, biological, and pharmaceutical processes. In particular, the recombinant production of high value proteins generally requires the isolation of a single valuable protein species from a highly complex mixture. For example, transformed cells may be grown in a suitable culture media, and the desired protein recovered from the growing cells, either by harvesting the cells and disrupting them to release the proteins or by collecting conditioned media into which the desired protein has been secreted. In both cases, it is necessary to recover and purify the desired protein from the cell culture.

Protein purification is most often achieved by chromatographic processes such as ion-exchange chromatography, size-exclusion chromatography, affinity chromatography, hydrophobic interaction chromatography, and the like. Usually, several separation steps will be performed sequentially in order to recover the desired protein at a required level of purity. Because of the high value of many protein products, particularly recombinant proteins, it is of great interest to provide separation methods and techniques which provide for enhanced purity and recovery from complex mixtures.

Heretofore, electrodialysis techniques have not found widespread use in the separation of proteins and other large molecules. Electrodialysis is a process for transferring ionic species from one solution to another across a membrane under the influence of a direct current electrical potential. Typically, such processes are performed in three-compartment cells defined by alternating anionic and cationic membranes. By passing a product stream between the alternate electrode pairs, and applying an electrical potential having the proper polarity, low molecular weight ionic species will be concentrated in dialysate streams which are directed between membranes which alternate with the product streams.

Electrodialysis techniques have not generally been used for separating one high molecular weight species from another high molecular weight species. While electrodialysis for protein fractionation has been described, such fractionation has been achieved indirectly by desalting a product stream so that certain protein(s) selectively precipitate out to enrich a fraction of remaining protein(s). No separation of proteins across a selective membrane is achieved.

It would therefore be desirable to provide improved electrodialysis methods and apparatus which are suitable for separating large molecular weight species, such as proteins, from one another. It would be particularly desirable if such methods and apparatus could selectively separate proteins into different process streams so that they could be separately collected and further processed. Such methods and apparatus should further be economic and be capable of providing high yields and purities of desired product streams.

2. Description of the Background Art

Electrodialysis for the separation of small ionic molecules is described in McRae, "Electrodialysis," in Kirk-Othmer, *Encyclopedia of Chemical Technology*, vol. 8, pp. 726–738, John Wiley & Sons, New York, 1986. Electrodialysis for the processing of proteins is described in Reed (1985) Genetic Engineering News vol. 5, no. 9, page 10. The purification of protein-containing whey solutions by electrodialysis is described in the following patents: U.S. Pat. Nos. 5,223,107; 4,441,978; 4,396,477; 4,351,710; 4,332,275; and 4,276,140. Other protein electrodialysis processes are described in WO 92/07818 and WO 91/12726. Isoelectric focusing techniques for separating proteins are described in Wenisch et al. (1992) Electrophoreses 13:668–673, and U.S. Pat. Nos. 5,082,548 and 4,971,670.

SUMMARY OF THE INVENTION

Electrodialysis methods and apparatus suitable for separating a charged first molecular species from a second molecular species are provided. The methods and apparatus are particularly useful for separating large (high molecular weight), charged molecular species, such a proteins, from one another, where separation is achieved by controlling the electrophoretic mobility of one or both of the species between and across semipermeable membranes. In particular, a load channel is formed between a retention membrane having a low molecular weight cutoff which passes neither of the molecular species and a separation membrane having a high molecular weight cutoff (at least three times that of the retention membrane, usually at least 10 times that of the retention membrane, and often much higher) which will pass at least one of the molecular species. By passing the product stream to be separated through the load channel, and a dialysate stream on the side of the separation membrane opposite to that of the product stream, selective passage of one of the molecular species through the separation membrane can be effected by applying an electric field having an appropriate polarity. The retention and/or separation membranes may also be charged (i.e., be anionic or cationic) in order to effect or enhance a desired separation.

In a broad aspect, the method of the present invention comprises flowing an aqueous media containing the species to be separated between the retention membrane and the separation membrane. The dialysate is flowed over the surface of the separation membrane opposite to the surface in contact with the aqueous media. By controlling electrical potential and differential pressure across the separation and retention membranes, one of the molecular species can be selectively passed through the separation membrane into the dialysate while the other of the molecular species is contained between the separation and retention membranes in the aqueous media.

In a first particular aspect of the method, an electrical potential is maintained to pass the charged first molecular species across the separation membrane into the dialysate. Optionally, the aqueous media may be maintained at an elevated pressure relative to the dialysate, causing a net flow of aqueous media through the membrane which will enhance transport of the charged first molecular species. The separation membrane will inhibit passage of the second molecular species. For example, the second molecular species may be charged oppositely to the charged first molecular species, allowing the separation membrane to be charged to selectively pass the first molecular species and inhibit passage of the second molecular species. Alternatively or additionally, the separation membrane may have a molecular weight cutoff which permits passage of the first molecular species but inhibits passage of the second molecular species.

With further regard to the first aspect of the present invention, a differential pressure across the separation membrane may be relied on primarily to effect transport of either the first molecular species or the second molecular species. Such a differential pressure will cause the net flow of aqueous media into the dialysate, and the separation membrane will be selective, i.e., permitting passage of the desired molecular species and inhibiting passage of the other molecular species. Such selectivity can be provided based on molecular weight cutoff, ionic selectivity (i.e., charge), or a combination of the two. Alternatively, the charged first molecular species may be maintained in aqueous media by applying an electrical potential having a polarity which causes the first molecular species to migrate toward the retention membrane. Such electrophoretic forces on the first charged molecular species will have to overcome the hydraulic transport of the species in the opposite direction resulting from the flow of aqueous media across the separation membrane. In many cases, it will be desirable to combine both selective membranes and electrophoretic isolation in order to maintain the first charged species within the aqueous media while transporting the second molecular species across the separation membrane.

In a second and preferred aspect of the method of the present invention, the aqueous media will be flowed through a plurality of parallel load channels and the dialysate will be flowed through a plurality of dialysate channels where the dialysate channels are interdigitated with the load channels. In this way, large volumes of the product stream to be separated can be processed economically. Other preferred aspects of the present invention include recycling of the aqueous media product streams and/or dialysate streams through the load channels and dialysate channels, respectively, and performing two or more separation steps in series.

Apparatus according to the present invention will comprise a pair of opposed electrodes including an anode and a cathode. At least one retention membrane is disposed between the opposed electrodes to define at least two cells. A separation membrane is disposed between the retention membrane and electrode in each cell to define the load channel and the dialysate channel in each of said cells. Separate manifolds are provided for flowing the aqueous media to the load channels and dialysate to the dialysate channels, and the apparatus may optionally further include pumps, pressure control equipment, pH control equipment, power supplies, and the like, for performing the method of the present invention. The electrodes and load channels are disposed relative to each other so that one of the molecular species will pass from the load channel through the separation membrane to the dialysate channel while the other molecular species remains within the load channel when an electrical potential is applied across the electrodes and/or differential pressure is applied across the separation membrane. The retention membrane will have a molecular weight cutoff which is low relative to the separation membrane. Typically, the molecular weight cutoff of the retention membrane will be from 200 D to 200 kD, usually being below 10 kD. The molecular weight cutoff of the separation membrane will be at least three times that of the retention membrane, typically being greater than 1 kD and up to a 2 $\mu$m pore size. Either or both of the retention membrane and the separation membrane may be charged to selectively pass or inhibit passage of the first charged molecular species, as described above, and optionally the second molecular species when charged.

Frequently, the retention membrane(s) and separation membranes will be oppositely charged to enhance separation in the methods of the present invention. For the separation of anionic proteins from the aqueous media, the separation membranes will be cationic (permitting passage of anionic species including the proteins) and the retention membranes will be anionic (blocking such passage). Conversely, for the separation of cationic proteins from the aqueous media, the separation membranes will be anionic and the retention membranes will be cationic.

The electrodialysis apparatus of the present invention may further comprise means for maintaining a differential pressure across the separation membranes, i.e., between the load channels and the dialysate channels. For example, a pressure control system can be provided for maintaining pressure within the load channels and dialysate channels at the desired differential. Usually, the electrodialysis apparatus will further include electrode isolation membranes, each having a low molecular weight cutoff, in order to isolate the electrodes from high molecular weight species in the product to be separated. More typically, the electrode isolation membrane adjacent the cathode will be cationic and the electrode isolation membrane disposed adjacent the anode will be anionic, in order to control the passage of low molecular weight ions to the electrodes.

Separation may further be effected by controlling the pH in the load channel(s), dialysate channel(s), or both. For example, by controlling the pH of the load channel to equal the isoelectric point of the second molecular species, the second molecular species will have no net charge and will be unaffected by an applied electric field. Thus, relation within the load channel will be enhanced. Conversely, by controlling the pH of the dialysate channel(s) to equal the isoelectric point of the first molecular species, retention of the first molecular species in the dialysate channel may be enhanced. Suitable pH controlling means will include titration devices for adding acids and bases as appropriate to maintain a desired pH value.

DESCRIPTION OF THE SPECIFIC EMBODIMENTS

Figure 1:
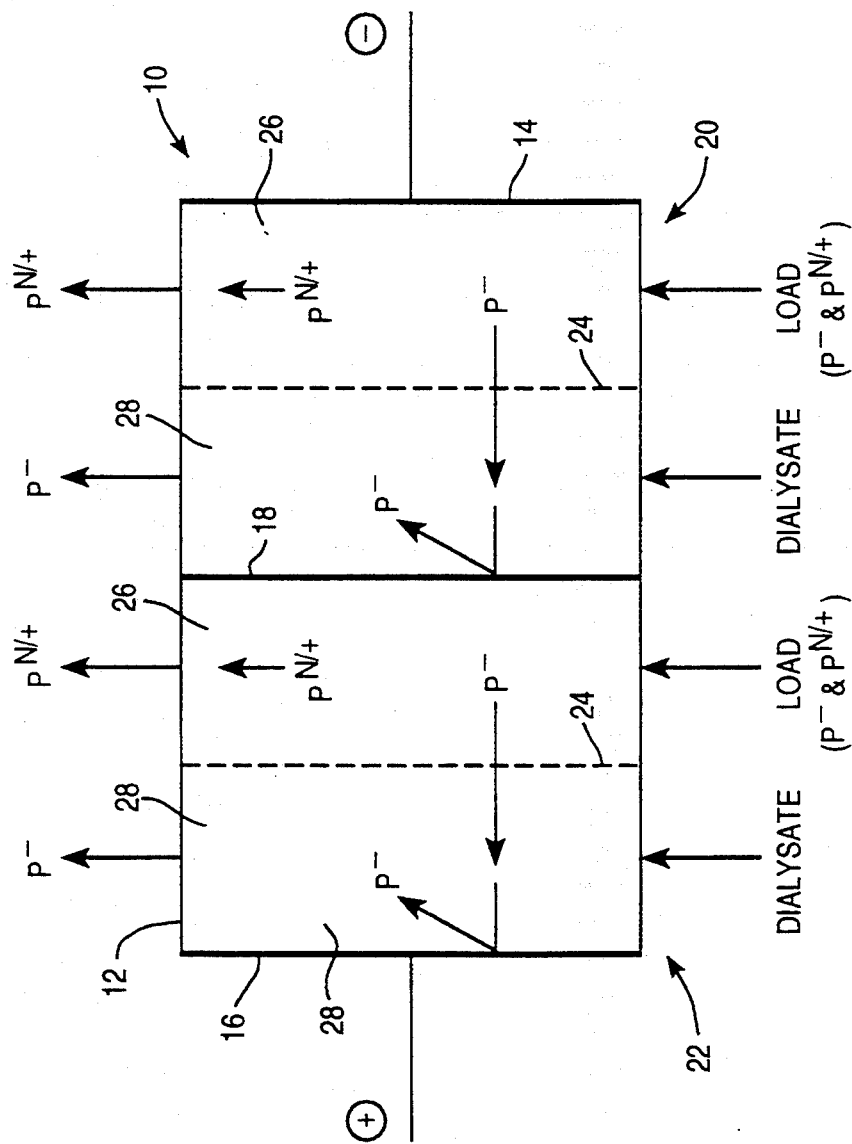
FIG. 1 illustrates a first exemplary method and apparatus according to the present invention where a negatively charged molecular species $P^-$ is separated from a neutral or positively charged species $P^{N/+}$ under the influence of an electrical potential.

The following description will be directed at the exemplary case of separating a first charged species from a second species (which may be charged or uncharged). It will be appreciated that a number of other molecular species will usually be present in the load stream which is to be separated. Depending on the specific nature of these other species, it may be possible to separate them in a desired manner, as part of the separation process described hereinafter. Alternatively, it may be desirable or necessary to separate these species by other techniques, either before or after separation according to the present invention is effected.

The separation methods and apparatus of the present invention are based on establishing a selective migration of proteins and/or other macromolecules across a separation membrane and between a load stream and a dialysate stream. Both the load stream and the dialysate stream will be flowing past the separation membrane, and migration of the molecular species to be separated is established by controlling electrical potential and differential pressure across the separation and retention membranes. Control of these parameters permits the selective passage of one of the molecular species across the separation membrane. Within certain embodiments of the invention, differential pressure is maintained at a level sufficient to provide a net flow of aqueous media through the separation membrane. Within other embodiments, substantially no differential pressure is present. Retention membranes are provided to contain the transported macromolecular species within the dialysate stream and non-transported macromolecular species within the load stream. Optionally, either or both of the separation and retention membranes may be charged in order to enhance selectivity and containment of the electrodialysis system.

Usually, the load stream and dialysate stream will flow in parallel, and the electric field will be perpendicular to the stream flow direction. It would be possible, however, to arrange the load stream and dialysate stream in counter-current or cross-current flow patterns so long as there is sufficient contact time and contact area for the proteins and/or other molecules to migrate across the separation membrane. Similarly, it would be possible to orient the electric field across the flowing streams at an angle other than 90° so long as there is a sufficient perpendicular component of the field to effect the desired migration of charged molecules (i.e., the electric field should not be parallel to the electrode surface and flow direction).

The electrodes and membranes will usually be planar and arranged in parallel to form a plurality of adjacent flow paths, where the flow paths may be parallel (flow directions differ by 0°), counter-current (flow directions differ by 180°), cross-current (flow directions differ by 90°), or any other relative angle, preferably being parallel. It may also be possible to utilize non-planar electrodes and/or membranes, such as concentric cylinders, nested spirals, and the like, so long as the desired relative orientations of aqueous media, dialysate flow, and electric field can be maintained.

The method and apparatus are particularly useful for separating a first charged species from a second molecular species, where both the first and second species are macromolecules having a molecular weight above 5 kD, usually above 10 kD, often above 50 kD, and sometimes above 100 kD, or higher. The present invention will be particularly suitable for separating proteins from other macromolecules, most usually from other proteins. The present invention permits the separation of proteins based on both size and net charge, where the net charge will depend at least in part on the pH of the load stream, dialysate stream, or both.

A primary use of the present invention will be in separating proteins from natural biological sources, particularly from cell culture, such as recombinant cell culture where a desired protein is expressed in bacteria, yeast, mammalian cells, or the like. A complex mixture of protein and other proteinaceous and non-proteinaceous components is obtained from such cell cultures, either by disruption of the cells or by recovery of conditioned media. Frequently, such complex mixtures will be subjected to initial separation techniques, such as the chromatographic techniques described above. The present invention is particularly useful for separating proteins which are close in size and other characteristics which render them difficult to separate by conventional separation techniques. Thus, the present invention will find use as a final or finishing separation technique for high purification of valuable protein products.

At least one of the molecular species to be separated will be charged. In the case of proteins, of course, charge is highly dependent on the pH of the solution in which the proteins are present. Every protein has an isoelectric point at which the net charge is zero and at which the electrophoretic ability of the protein is zero. Below the isoelectric pH, the protein is positively charged so that it will migrate toward the anode in an applied electric field. At a pH above the isoelectric pH, the protein is negatively charged so that it will migrate toward the cathode in an applied electric field. Thus, in all of the methods described hereinafter, it will be possible to affect separation based on the pH of the load stream and/or the dialysate stream. That is, the direction of electrophoretic migration of a given protein within an applied electric field will depend on both pH of the aqueous medium in which it is present and on the polarity of the field. Moreover, by maintaining the pH of the load stream and/or dialysate stream at the isoelectric point of one of the species to be separated, retention of that species within the stream can be enhanced.

Membranes used in the methods and apparatus of the present invention will be semipermeable with molecular weight cutoffs chosen to selectively pass or inhibit passage of the molecular species to be separated. The membranes will be of ordinary construction and composition, with conventional microfiltration membranes, ultrafiltration membranes, and reverse osmosis membranes being suitable, depending on the desired molecular weight cutoff. For example, microfiltration membranes typically have a pore size in the range from about 0.05 $\mu$m to 2 $\mu$m. Ultrafiltration membranes have a smaller pore size with a molecular weight cutoff in the range from about 1 kD to 500 kD. Reverse osmosis membranes have a very small pore size with a molecular weight cutoff typically below 2 kD, and usually below 1 kD. Such membranes are available from suppliers such as Millipore Corp., Bedford, Mass.; Cuno, Meriden, Conn.; Electrosynthesis Co., Inc., E. Amherst, N.Y.; Filtran Technology Corp., Northborough, Mass.; Aldrich Chemical Co., Milwaukee, Wis., and the like. Retention membranes will have a lower molecular weight cutoff, typically being 200 D to 200 kD, preferably being below 10 kD. Separation membranes will have a molecular weight cutoff at least three times that of the retention membranes, usually being in the range from 600 D to 1,000 kD, preferably being above 10 kD.

The separation and retention membranes of the present invention may also be charged in order to further effect or enhance separation of the molecular species based on charge. Suitable ion-selective membranes will have low electrical resistance, good mechanical strength, and good chemical stability. Usually, the membranes will be composed of a synthetic polymeric backbone having charged moieties which impart the ionic selectivity. Cation-selective membranes will have a fixed, negative charge with positive counter ions being mobile in an applied aqueous media. In contrast, anion-selective membranes will have a net positive charge with negative counter ions being mobile in an applied aqueous media. A charged molecular species will thus be able to pass through the ion-selective membrane by exchange with the mobile counter ions having a like charge. The most suitable membranes will be reinforced with woven, synthetic fabrics to improve mechanical properties.

The present invention will employ electrical power supplies in order to apply a direct current electrical potential across the separation and retention membranes. The applied power will typically be in the range from 50 amps/m$^2$ to 500 amps/m$^2$, based on electrode area. The applied voltage will usually be from 5 to 500 volts/separation membrane preferably from 20 to 200 volts/separation membrane. The electrodes may be formed from any conventional electrode material, including stainless steel, and the like. In the examples described hereinafter, a stabilized electrode material designated DSA, from the Electrosynthesis Co. was employed.

Referring now to the drawings, FIGS. 1-4 illustrate alternative embodiments and configurations for the method and apparatus of the present invention. These figures show the basic relationship between electrodes, separation membranes, retention membranes, and dialysate and load flows in order to demonstrate the principles of the present invention. It will be appreciated that systems for performing the method of the present invention in a practical and commercial manner will frequently employ additional structure, as at least partially discussed in connection with FIG. 5 hereinafter.

Referring now in particular to FIG. 1, electrodialysis unit 10 comprises a chamber 12 having an anode 14 at one end and an opposed cathode 16 at an opposite end. Electrodes 14 and 16 are in the form of flat plates which define a working volume therebetween. A flat retention membrane 18 is disposed to divide the working volume into two cells 20 and 22. A flat separation membrane 24 is disposed within each cell and divides the cell into a load channel 26 and a dialysate channel 28. The use of flat, parallel electrodes and membranes is particularly convenient and simplifies explanation of workings of the present invention, but is not essential. Other membrane and/or electrode geometries may also find uses, such as concentric cylinders, nested spirals, and the like.

The electrodialysis unit 10 is configured to separate a negatively charged molecular species P$^-$ from a neutral or positively charged molecular species p$^{N/+}$. An aqueous mixture of the two species (which may be present with other low and/or high molecular weight species) is introduced into each of the load channels in parallel, and a dialysate media is introduced into each of the dialysate channels in parallel. By applying an electric field with the polarity indicated, the negatively charged species is caused to migrate to the left (as illustrated in FIG. 1) toward the cathode. Separation membrane 24 will have a sufficiently high molecular weight cutoff to permit passage of the negatively charged species. The neutral or positively charged species P$^{N/+}$ will remain within the load channel, with positively charged species migrating toward the anode 14 (but remaining contained within the load channels by the low molecular weight cutoff retention membrane 18 and anode 14, respectively).

Optionally, the load channels 26 may be maintained at a pressure which is higher than that of the dialysate channels 28. In this way, a net flow of aqueous media from the load channels will pass through the separation membranes 24 into the dialysate channels 28. Such liquid flow will enhance the transport of the P$^-$ species through the membrane. The other species P$^{N/+}$ will be too large to pass through the separation membrane 24 and/or (in the case of positively charged species) will be maintained within the load channel by virtue of the applied electric field.

Figure 2:
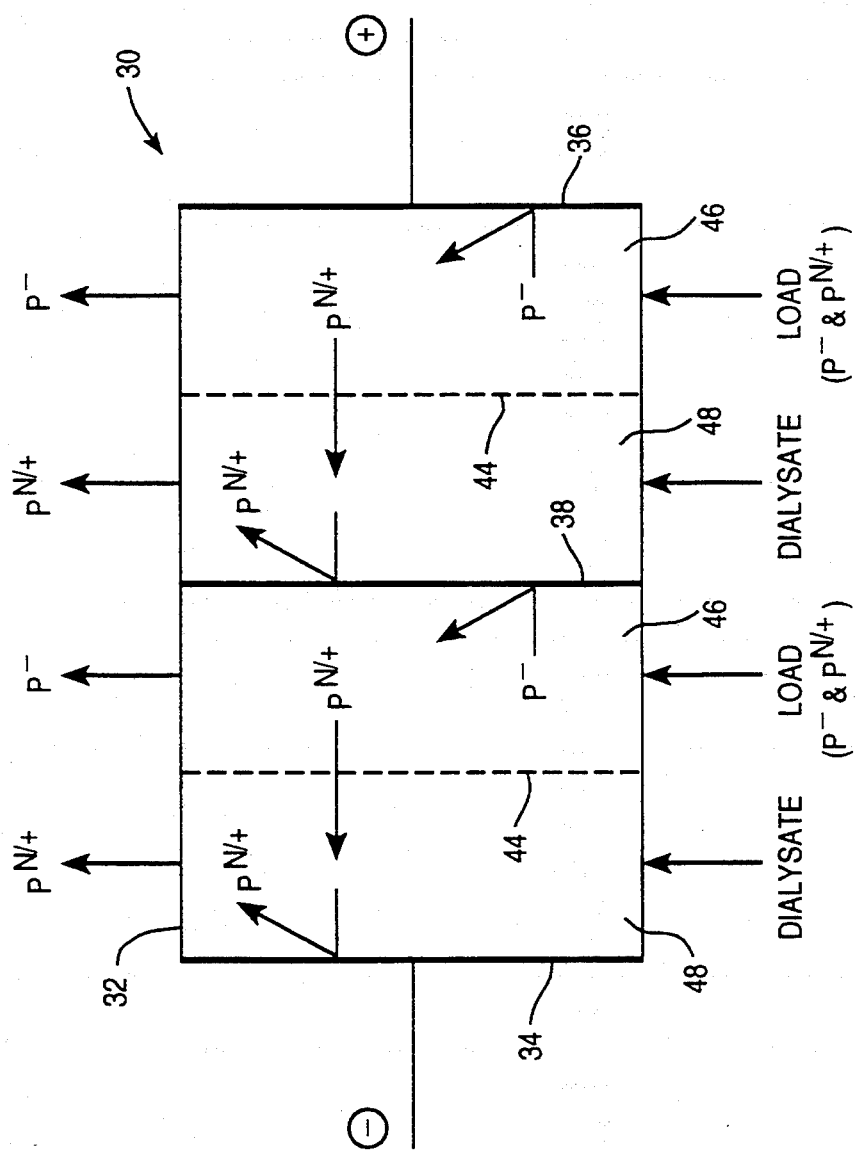
FIG. 2 illustrates a second exemplary method and apparatus according to the present invention where a neutral or positively charged molecular species $P^{N/+}$ is separated from a negatively charged species $P^-$ under a pressure gradient where the charged species $P^-$ is maintained in the load channel by an electrical potential.

Referring now to FIG. 2, a second electrodialysis unit 30 comprising a chamber 32, an anode 34, a cathode 36, a retention membrane 38, and two separation membranes 44 is illustrated. A load stream containing a negatively charged species P$^-$ and a neutral or positively charged species P$^{N/+}$ is directed down parallel load channels 46. Dialysate streams are concurrently directed down parallel dialysate channels 48. Pressure in the load channels 46 is elevated above that in the dialysate channels 48, typically by differential pressure in the range from about 0.1 psi to 15 psi, causing a net flow of aqueous media from the load channel to the dialysate channel. The flow of aqueous media will carry the molecular species P$^{N/+}$ through the membrane, even in the absence of an applied electric field. In order to prevent passage of the negatively charged species P$^-$, however, an electric field is applied with the indicated polarity. So long as the electric field is sufficiently strong to overcome the hydraulic forces on P$^-$, the P$^-$ species will be maintained within the load channel, while the species $P^{N/+}$ separates into the dialysate channel. In the case of a positively charged $P^{N/+}$, the electric field will enhance separation across the separation membrane 44 due to electrophoretic mobility.

The electrodialysis units 10 and 30, as thus far described, would function with neutrally-charged membranes. That is, the membranes need not be either cationic-selective nor anionic-selective in order to effect the separations described. Optionally, either or both of the separation or retention membranes could be anion-selective or cation-selective in order to further enhance the desired separations.

Figure 3:
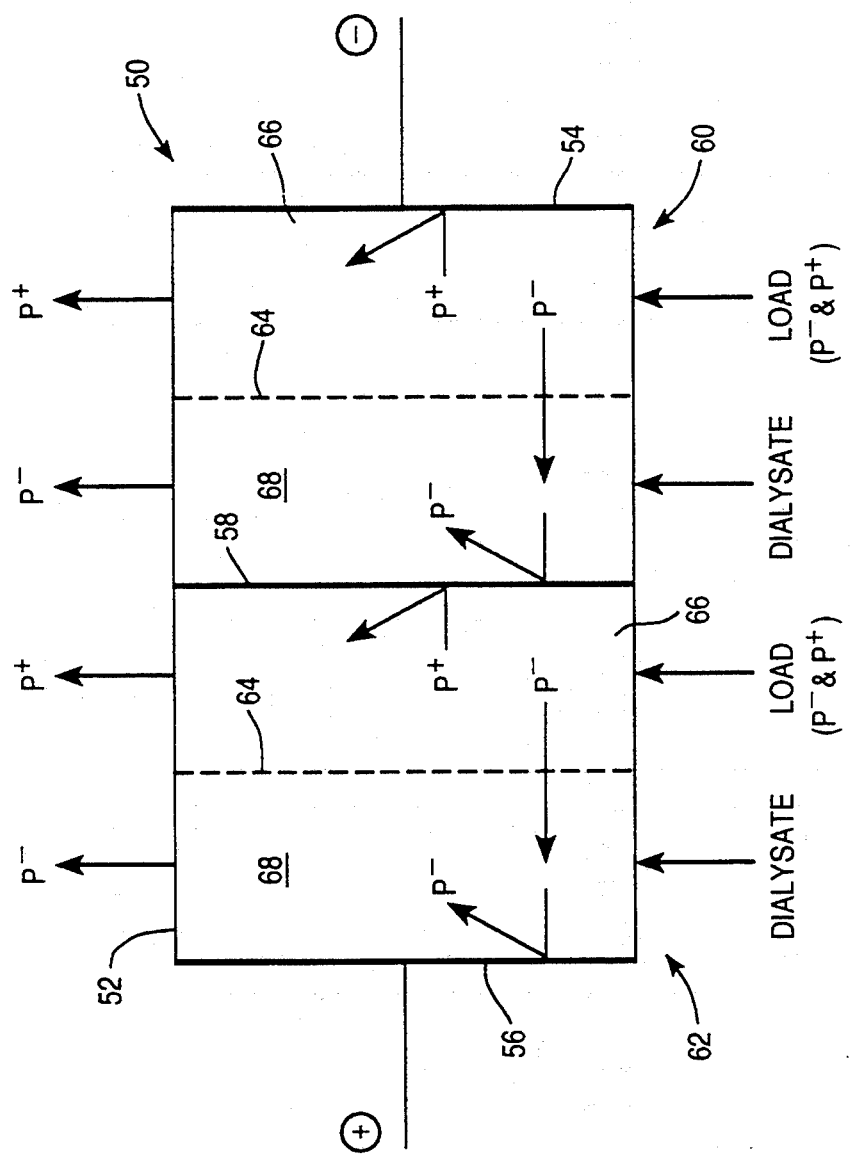
FIG. 3 illustrates a third exemplary method and apparatus according to the present invention where oppositely charged molecular species $P^-$ and $P^+$ are separated across charged separation membranes and retention membranes under the influence of an electrical potential.

Referring now to FIG. 3, an electrodialysis unit 50 which employs charged membranes in order to enhance separation will be described. The electrodialysis unit 50 includes a chamber 52 having an anode 54 and a cathode 56 at opposite ends thereof. A retention membrane 58 will have a negative charge under the expected conditions of use. By virtue of its negative charge, the membrane will be cation-selective, i.e., allow passage of cations but inhibit passage of anions. Separation membranes 64 will be cationic, i.e., have a positive charge which permits the passage of negatively charged species but inhibits the passage of positively charged species.

A load including a negatively charged species $P-$ and a positively charged species $P+$ is flowed through load channels 66. With the illustrated polarity of the electrodes, the negatively charged species $P-$ migrates toward the left, i.e., toward cathode 56, while the positively charged species $P+$ migrates toward the anode 54. The separation membrane permits passage of the negatively charged species $P-$, but will inhibit passage of the positively charged species $P+$. The negatively charged retention membrane 58 prevents further migration of the negatively charged species $P-$ from the dialysate channel 68 of the first cell 60. The retention membrane 58 also has a sufficiently low molecular weight cutoff to prevent further migration of the positively charged species $P+$ from the load channel 66 of the second cell 62. Optionally, although not necessarily, a differential pressure may be maintained between the load channels 66 and the dialysate channels 68 in order to further enhance separation of the molecular species.

Figure 4:
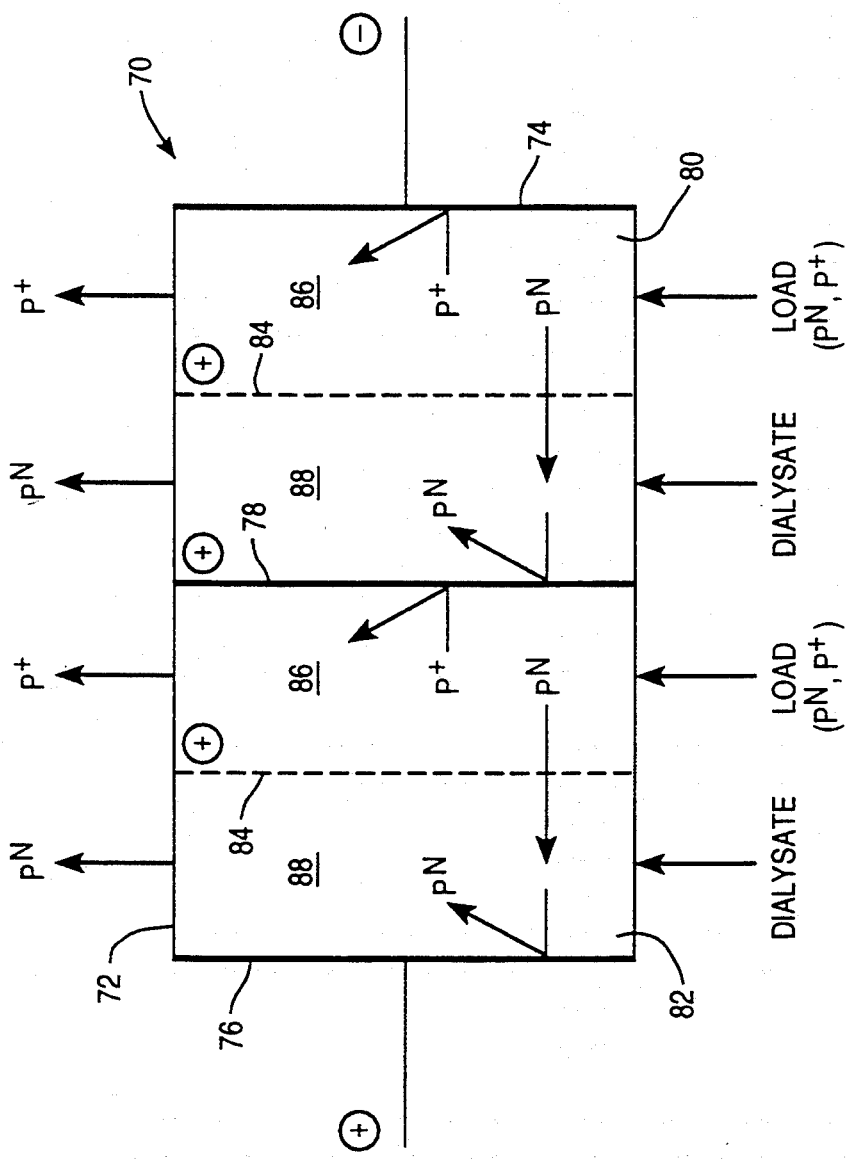
FIG. 4 illustrates a fourth exemplary method and apparatus according to the present invention where a neutral molecular species $P^N$ is separated from a positively charged molecular species $P^+$ by application of a differential pressure where the molecular species $P^+$ is maintained in the load channel by a combination of electrical potential field and size and charge-selective membranes.

Referring now to FIG. 4, method and apparatus for separating a neutral species $P^N$ and a positively charged species $P+$ utilizing differential pressure as a driving force is illustrated. An electrodialysis unit 70 comprises a chamber 72 having an anode 74 and a cathode 76. A positively charged retention membrane 78 divides the apparatus into a first cell 80 and a second cell 82. The separation membranes 84 are also positively charged and disposed in each cell, defining load channels 86 and dialysate channels 88.

The load flows into each load channel 86, where the neutral species $P^N$ passes into the dialysate channel by virtue of a pressure differential. Passage of the positive species $P+$ through the separation membranes 84 is inhibited by maintenance of the electric field with the indicated polarity. The positive species $P+$ moves in a direction opposite to the flow of aqueous media through the separation membrane. The positively charged retention membrane helps prevent passage of the positively charged species $P+$ from the load channel of cell 82 to the dialysate channel of cell 80. Such ionic selectivity, however, is not necessary so long as the molecular weight cutoff of the retention membrane 78 is sufficiently low.

Figure 5:
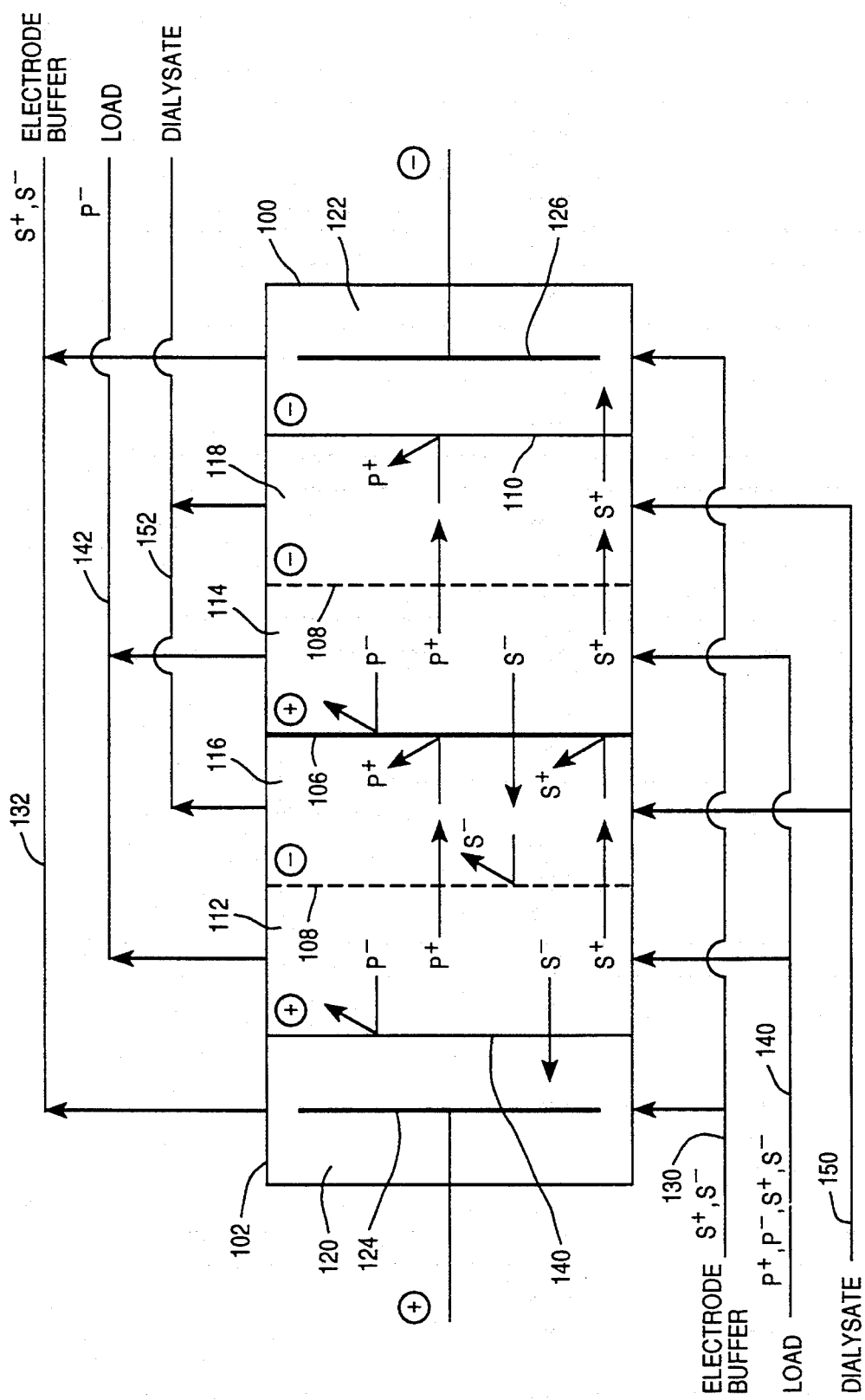
FIG. 5 illustrates a fifth exemplary method and apparatus according to the present invention, where additional components of a preferred apparatus are shown.

Referring now to FIG. 5, an electrodialysis unit 100 comprises a chamber 102 having a working volume including a cathode isolation membrane 104, a retention membrane 106, a pair of separation membranes 108, and an anode isolation membrane 110. The membranes are arranged to provide a pair of parallel load channels 112 and 114, a pair of parallel dialysate channels 116 and 118 which are interdigitated with the load channels, a cathode compartment 120, and an anode compartment 122. Cathode 124 is disposed within the cathode compartment 120 and anode 126 is disposed within the anode compartment 122. In this way, an electrical potential can be applied across the entire assembly of membranes as just described.

An electrode buffer is delivered to the cathode compartment 120 and anode compartment 122 via a manifold 130 and is collected from said compartments by a second manifold 132. Similarly, load containing a positively charged species Phu + and a negatively charged species $P-$ to be separated is delivered to the load channels 112 and 114 through a manifold 140 and collected through a second manifold 142. Usually, the load will contain other charge species, such as small mobile ions $S+$ and $S-$, typically in the form of salts. Dialysate is delivered to the dialysate channels 116 and 118 through a manifold 150 and collected in a second manifold 152.

In operation, an electrode buffer is continuously delivered to both the cathode chamber 120 and anode chamber 122. The electrode buffer will provide additional mobile ions $S+$ and $S-$ which provide for the necessary current flow to maintain the desired electrical potential across the cell. A wide variety of buffers will be suitable, particularly common biological buffers, such as Tris-acetate, and the like. Typically, the electrode buffer will be recycled through a heat exchanger in order to remove generated heat.

The load containing the molecular species to be separated is delivered to the parallel load channels 112 and 114 while the dialysate is simultaneously delivered to the dialysate channels 116 and 118. By maintaining the indicated electrical potential, the positively charged species will pass through the negatively charged separation membranes and be retained within dialysate channel 116 by retention membrane 106 and within dialysate channel 118 by anode membrane 110. The positive charge on the retention membrane will further act to prevent passage of the positively charged species $P+$. The negatively charged species $P-$ in load channel 114 is prevented from passing through the retention membrane 106 by the relatively low molecular weight cutoff. The mobile ions $S+$ and $S-$ are sufficiently small to pass through all of the membranes and hence will be able to circulate with the electrode buffer. A certain portion of the mobile ions, however, will be carried over with the flowing load and dialysate streams. The separation results in concentration of negatively charged species $P-$ in the load stream and concentration of the positively charged species $P+$ in the dialysate stream. It will be appreciated, of course, that complete separation will not be achieved in a single pass through the electrodialysis unit 100.

Figure 6:
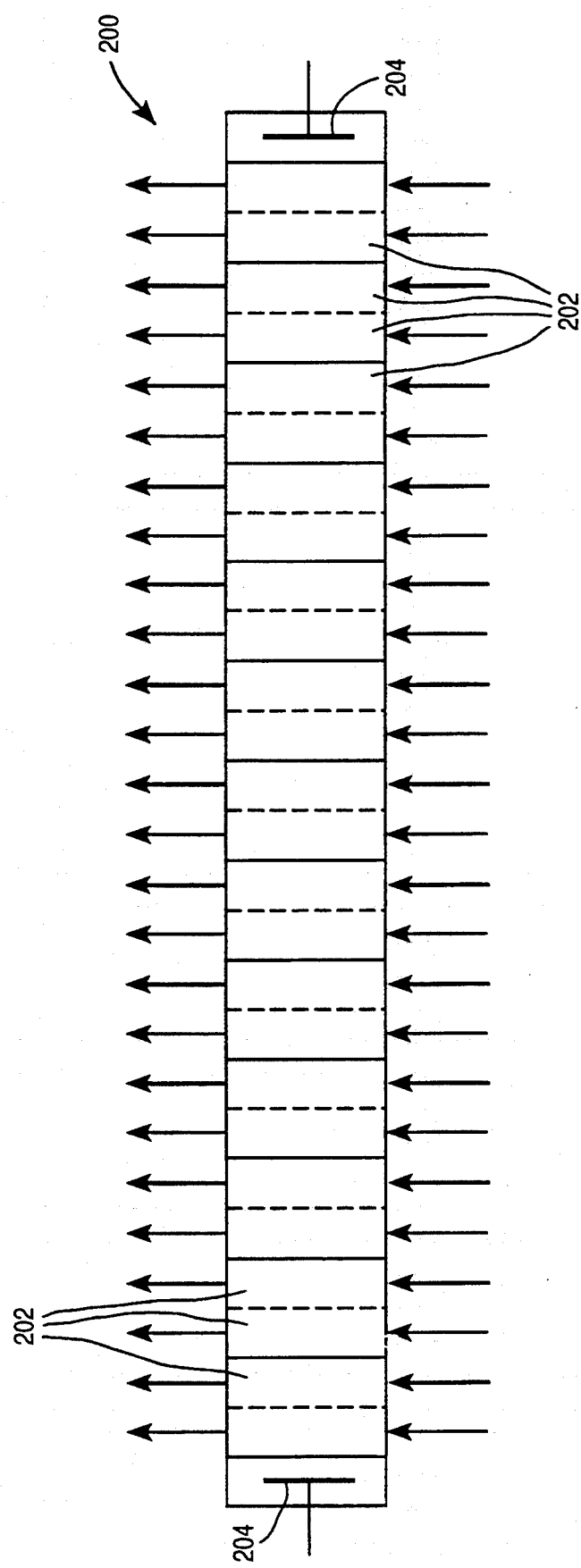
FIG. 6 illustrates apparatus according to the present invention comprising a number of parallel electrolytic cells.

In order to improve through-put of the electrodialysis units of the present invention, an electrodialysis unit 200 (FIG. 6) may be constructed comprising the plurality of cells 202 disposed in parallel between electrodes 204. Conveniently, as many as 50 cells or more may be provided in parallel in order to provide industrial-scale equipment.

Figure 7:
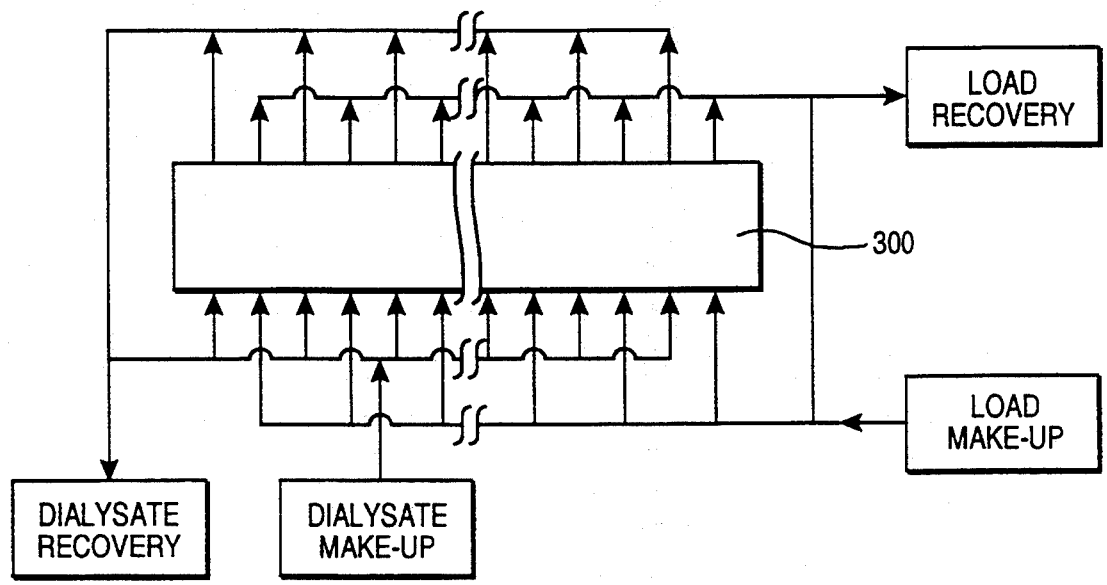
FIG. 7 illustrates the method and apparatus of the present invention employing recycling of the dialysate in load streams.

Referring now to FIG. 7, recovery and purity of either or both of the species to be separated may be achieved through recycling the load streams and dialysate streams through a single electrodialysate unit 300. A portion of the dialysate and load stream can be continuously withdrawn in order to recover product. The volume will be made up with fresh dialysate and load streams in order to maintain a continuous process.

Figure 8:
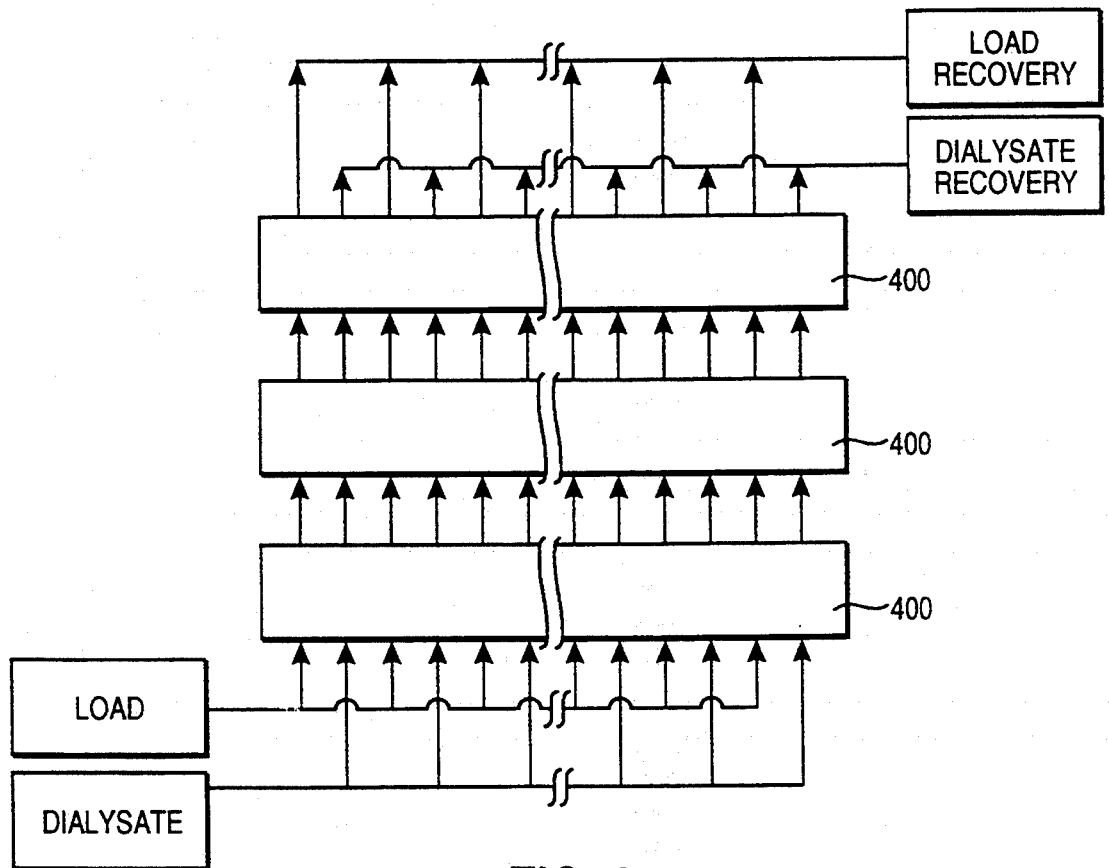
FIG. 8 illustrates the method and apparatus of the present invention employing multiple separation steps in series.

Referring now to FIG. 8, recovery and purity can further be enhanced by providing a plurality of electrodialysate units 400 in series with each state providing improved recovery and purity.

EXPERIMENTAL

Material and Methods

Bovine hemoglobin (10 g/l; Sigma Chemical Co., St. Louis, Mo.) and bovine serum albumin (BSA; 10 g/l; Sigma Chemical Co.) were combined in 20 mM Tris-acetate at pH 6.3, where hemoglobin (isoelectric point 7.2) has a net positive charge and BSA (isoelectric point 5.2) has a net negative charge. The dialysate was 20 mM Tris-acetate, pH 5.3, and the electrode buffer was 20 mM Tris-acetate, pH 6.0.

Figure 9:
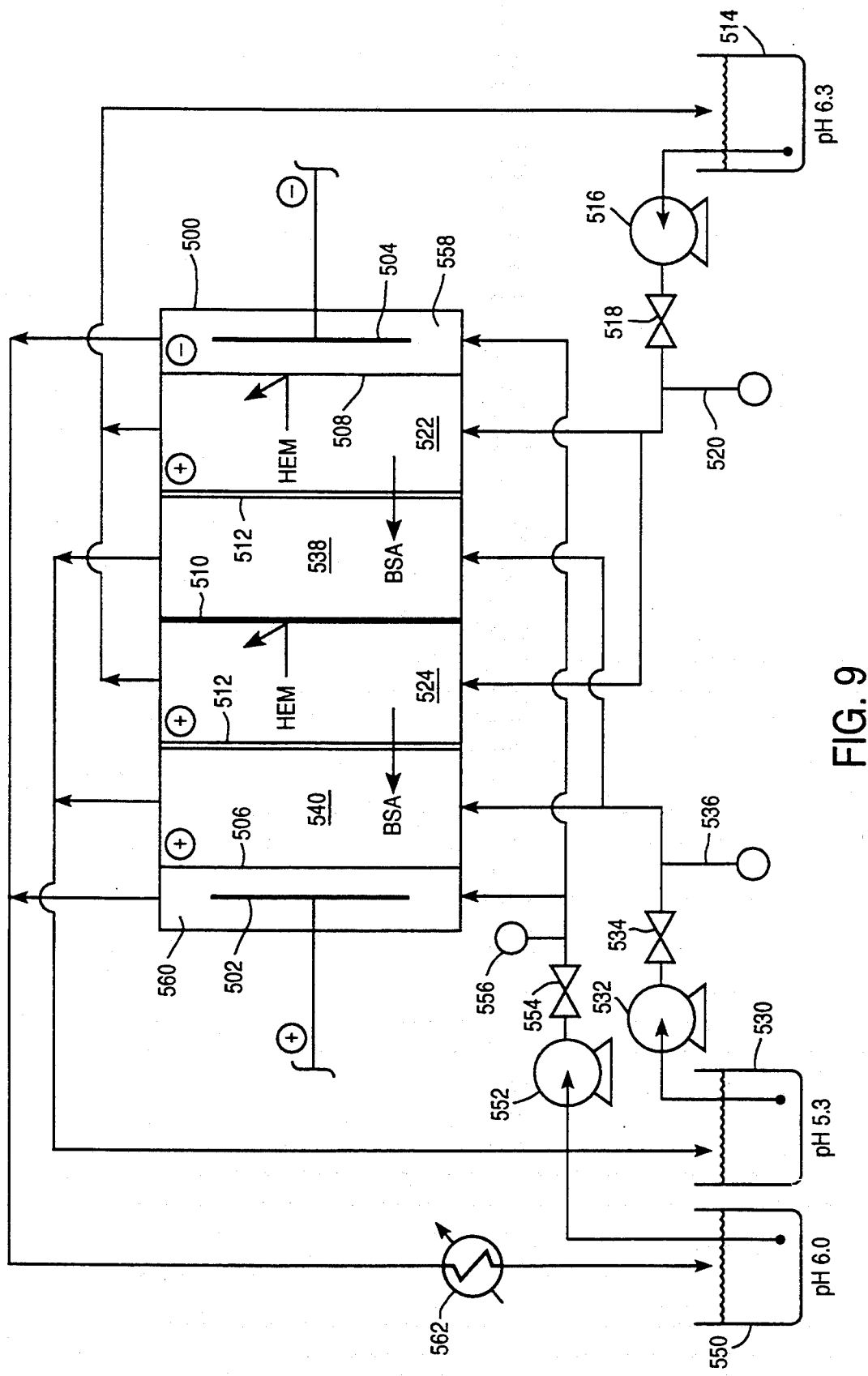
FIG. 9 illustrates an experimental apparatus utilized in the examples described in the Experimental section hereinafter.

Apparatus included an electrodialysis module 500 (Electrosynthesis MP-cell, Electro Cell AB, Sweden) having a 316 SS cathode 502 and a DSA anode 504, as illustrated in FIG. 9. The cathode membrane 506 was a Neosepta AMX membrane (Electrosynthesis Co., Inc., E. Amherst, N.Y.), and the anode membrane 508 was a Neosepta CMS (Electrosynthesis Co., Inc.). The retention membrane 510 was an Omega 1000 (Filtran Technology Corp., Northborough, Mass.). Two separation membranes 512 were Cuno 1054 (Cuno, Meriden, Conn.). Membrane areas were 100 cm² and spacing between membranes was 0.5 mm. Other membrane characteristics were as follows:

| Membrane | Selectivity | MW Cutoff |
| --- | --- | --- |
| Cathode 506 | Cationic | 200 D |
| Anode 508 | Anionic | 200 D |
| Retention 510 | Uncharged | 1 kD |
| Separation 512 | Cationic | 0.1 μm pore size |

A load flow circuit included a recirculation tank 514 which was initially charged with approximately 16 of the hemoglobin-BSA mixture. A recirculation pump 516 (Cole-Parmer Instrument Co., Chicago, Ill., #G-68920-00) directed flow through a pressure gate 518 and past pressure gauge 520 through a manifold into load channels 522 and 524. Flow from the load channels 522 and 524 was collected in a manifold and returned to the recirculation tank 514. pH was maintained at 6.3 in the recirculation tank by titration with NaOH and acetic acid.

A dialysate flow circuit included a recirculation tank 530 which was initially charged with 1 l of dialysate. A recirculation pump 532 (Cole-Parmer #G-07142-02) directed flow through a pressure gate 534 (Cole-Parmer #G-68920-00) and past pressure gauge 536 through a manifold into dialysate channels 538 and 540. Flow from the dialysate channels 538 and 540 was collected in a manifold and returned to the recirculation tank 530. pH was maintained at 5.3 in the recirculation tank 530 by titration with NaOH and acetic acid.

An electrode buffer flow circuit included a recirculation tank 550 which was initially charged with 1.5 l of electrode buffer. A recirculation pump 552 (Cole Parmer #G-07142-02) directed flow through a pressure gate 554 (ColeParmer #G-68920-00) and past pressure gauge 556 through a manifold into anode chamber 558 and cathode chamber 560. Flow from the anode and cathode chambers was collected in a manifold and passed through a heat exchanger 562 (10 inch, CAL-GLASS, Costa Mesa, Calif.) to maintain a temperature below 30° C. pH was maintained at 6.0 by titration with NaOH and acetic acid.

The pumps were run to maintain the following recirculation rates:

| FLOW RATE | |
| --- | --- |
| Load | 40 l/hr |
| Dialysate | 20 l/hr |
| Electrode Buffer | 20 l/hr |

The pressure in the load channels 522 and 524 was maintained at about 1.6 psi, while the pressure in the dialysate channels was maintained at about 0.6 psi. The differential pressure of approximately 1 psi resulted in a net flow of load into the dialysate. An electrical potential of 160 VDC was maintained across the cathode 502 and anode 504 using an EC 570 power supply (EC Apparatus Corp., St. Petersburg, Fla.). The yield/purity of hemoglobin and BSA were determined by spectrophotometry in the load and dialysate, respectively, based on the ratio of absorbance at 280 nm and 400 nm ($A_{280}/A_{400}$).

Results

Figure 10:
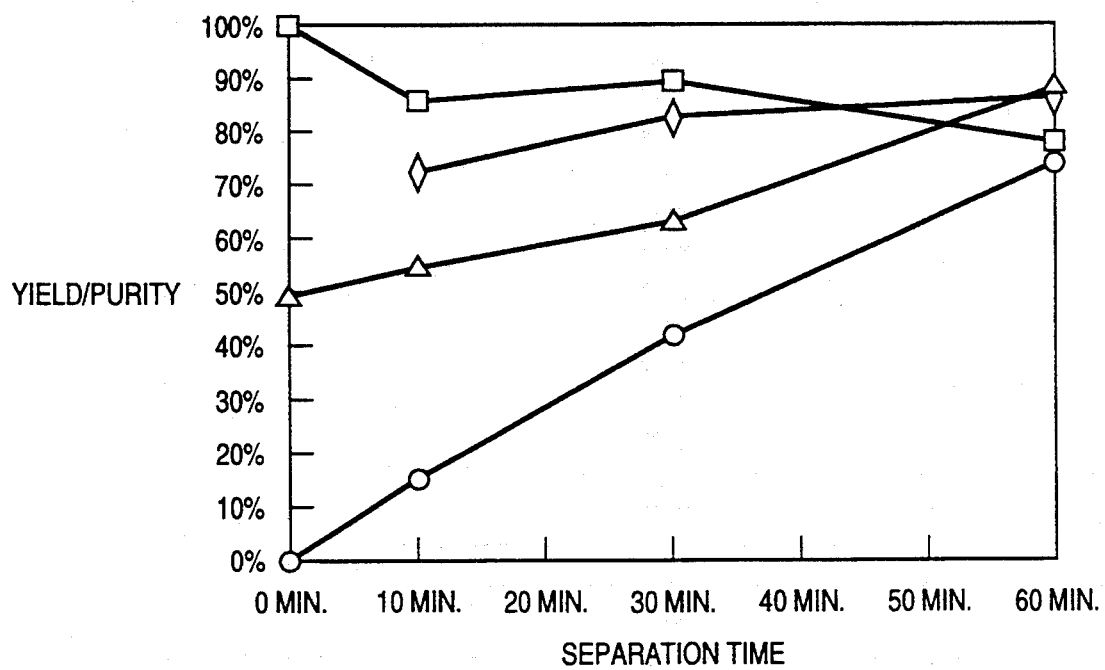
FIG. 10 is a graph illustrating the yield and purity of hemoglobin in the load stream and yield and purity of bovine serum albumin in the dialysate stream of the experimental apparatus of FIG. 9 over time.

Electrodialysis of the hemoglobin/BSA mixture resulted in selective separation of the BSA from the load, across the separation membranes 512, into the dialysate, as shown in FIG. 10. The yield of BSA in the dialysate (■) rose from 0% at 0 min. to above 70% at 60 min., while BSA purity in the dialysate (♦) rose from about 72% at 10 minutes to over 80% at 60 min. Hemoglobin purity in the load (▲), which began at 50% at 0 min., rose to over 80% at 60 min., while hemoglobin yield in the load (□) fell to about 80%. For this system, power consumption was about 40 kw-hr./kg BSA and capacity was 253 g BSA/m²-hr. Thus, separation of proteins and other charged macromolecules can be achieved by electrodialysis according to the present invention.

Although the foregoing invention has been described in some detail by way of illustration and example, for purposes of clarity of understanding, it will be obvious that certain changes and modifications may be practiced within the scope of the appended claims.

What is claimed is:

1. A method for separating a charged first molecular species from a second molecular species in an aqueous media, said method comprising:

flowing the aqueous media between a retention membrane having a low molecular weight cutoff and a separation membrane having a high molecular weight cutoff, wherein both the first molecular species and the second molecular species have molecular weights of over 5 kD, and wherein the high molecular weight cutoff is at least three times the low molecular weight cutoff and the separation membrane will pass at least one of the first and second molecular species and the low molecular weight cutoff of the retention membrane will pass neither of the molecular species;

flowing dialysate over a surface of the separation membrane opposite to the surface in contact with the aqueous media flow; and controlling electrical potential and differential pressure across the separation and retention membranes in order to selectively pass one of the molecular species through the separation membrane into the dialysate and contain the other of the molecular species between the separation and retention membranes in the aqueous media.

2. A method as in claim 1, wherein an electrical potential is maintained to pass the charged first molecular species across the separation membrane into the dialysate.

3. A method as in claim 2, wherein pH of the aqueous media is controlled at an isoelectric point of the second species to enhance retention of the second species in the aqueous media.

4. A method as in claim 2, wherein pH of the dialysate is controlled at an isoelectric point of the first charged molecular species to neutralize the charge and enhance retention of the first species in the dialysate.

5. A method as in claim 2, wherein there is substantially no differential pressure across the separation membrane.

6. A method as in claim 2, wherein a differential pressure is maintained so that aqueous media flows through the separation membrane into the dialysate to enhance transport of the charged first molecular species and wherein the separation membrane inhibits passage of the second molecular species.

7. A method as in claim 6, wherein the second molecular species is charged oppositely to the first molecular species and wherein the separation membrane is charged to selectively pass the first molecular species and inhibit passage of the second molecular species.

8. A method as in claim 6, wherein the separation membrane has a molecular weight cutoff which permits passage of the first molecular species but not the second molecular species.

9. A method as in claim 8, wherein the separation membrane is uncharged.

10. A method as in claim 8, wherein the second molecular species is charged oppositely to the first molecular species and wherein the separation membrane is charged to selectively pass the first molecular species and inhibit passage of the second molecular species.

11. A method as in claim 1, wherein a differential pressure is maintained so that aqueous media flows through the separation membrane and carries the second molecular species into the dialysate and wherein an electrical potential is maintained to retain the charged first molecular species against the retention membrane.

12. A method as in claim 1, wherein a differential pressure is maintained so that aqueous media flows through the separation membrane and carries said one of the molecular species into the dialysate and wherein the separation membrane inhibits passage of the other of the molecular species.

13. A method as in claim 12, wherein said one of the molecular species is the charged first molecular species and wherein an electrical potential is maintained to enhance transport of the first charged molecular species across the separation membrane.

14. A method as in claim 13, wherein the second molecular species is charged oppositely to the first molecular species and wherein the separation membrane is charged to selectively pass the first molecular species and inhibit the second molecular species.

15. A method as in claim 12, wherein said one of the molecular species is the second molecular species and wherein an electrical potential is maintained to inhibit passage of the charged first molecular species across the separation membrane.

16. A method as in claim 15, wherein second molecular weight species is charged oppositely to the first molecular species and wherein the separation membrane is charged to selectively pass the second molecular species and inhibit the first molecular species.

17. A method as in claim 16, wherein at least one of the molecular species is a protein.

18. A method as in claim 1, wherein at least one of the molecular species is a protein.

19. A method as in claim 1, wherein both the first and second molecular species are proteins.

20. A method as in claim 1, wherein a ratio of the weight of the first molecular species to the weight of the second molecular species is more than $\frac{1}{3}$ and less than 3.

21. A method for separating a charged first molecular species from a second molecular species in an aqueous media, said method comprising:

flowing the aqueous media through a plurality of parallel load channels;

flowing a dialysate through a plurality of dialysate channels, wherein the dialysate channels are interdigitated with the load channels and separated therefrom on a first side by a separation membrane having a high molecular weight cutoff and on a second side by a retention membrane having a low molecular weight cutoff, wherein both the first molecular species and the second molecular species have molecular weights of over 5kD, and wherein the high molecular weight cutoff is at least three times the low molecular weight cutoff and the separation membrane will pass at least one of the first and second molecular species and the low molecular weight cutoff of the retention membrane will pass neither of the molecular species; and controlling electrical potential and differential pressure across the separation membranes in order to selectively pass one of the molecular species from the load channel through the separation membrane into the dialysate while containing the other of the molecular species in the load channel.

22. A method as in claim 21, wherein an electrical potential is maintained to pass the charged first molecular species across the separation membrane into the dialysate.

23. A method as in claim 22, wherein pH of the aqueous media is controlled at an isoelectric point of the second species to enhance retention of the second species in the aqueous media.

24. A method as in claim 22, wherein pH of the dialysate is controlled at an isoelectric point of the first charged molecular species to neutralize the charge and enhance retention of the first species in the dialysate.

25. A method as in claim 22, wherein there is substantially no differential pressure across the separation membrane.

26. A method as in claim 22, wherein a differential pressure is maintained so that aqueous media flows through the separation membrane into the dialysate channels to enhance transport of the charged first molecular species and wherein the separation membrane inhibits passage of the second molecular species.

27. A method as in claim 26, wherein the second molecular species is charged oppositely to the first molecular species and wherein the separation membrane is charged to selectively pass the first molecular species and inhibit passage of the second molecular species.

28. A method as in claim 26, wherein the separation membrane has a molecular weight cutoff which permits passage of the first molecular species but not the second molecular species.

29. A method as in claim 28, wherein the separation membrane is uncharged.

30. A method as in claim 28, wherein the second molecular species is charged oppositely to the first molecular species and wherein the separation membrane is charged to selectively pass the first molecular species and inhibit passage of the second molecular species.

31. A method as in claim 21, wherein a differential pressure is maintained so that aqueous media flows through the separation membrane and carries the second molecular species into the dialysate and wherein an electrical potential is maintained to retain the charged first molecular species against the retention membrane.

32. A method as in claim 21, wherein a differential pressure is maintained so that aqueous media flows through the separation membrane and carries said one of the molecular species into the dialysate and wherein the separation membrane inhibits passage of the other of the molecular species.

33. A method as in claim 32, wherein said one of the molecular species is the charged first molecular species and wherein an electrical potential is maintained to enhance transport of the first charged molecular species across the separation membrane.

34. A method as in claim 33, wherein the second molecular species is charged oppositely to the first molecular species and wherein the separation membrane is charged to selectively pass the first molecular species and inhibit the second molecular species.

35. A method as in claim 32, wherein said one of the molecular species is the second molecular species and wherein an electrical potential is maintained to inhibit passage of the charged first molecular species across the separation membrane.

36. A method as in claim 35, wherein the second molecular species is charged oppositely to the first molecular species and wherein the separation membrane is charged to selectively pass the second molecular species and inhibit the first molecular species.

37. A method as in claim 21, wherein both the first and second molecular species are proteins.

38. A method as in claim 21, wherein a ratio of the weight of the first molecular species to the weight of the second molecular species is more than ⅓ and less than 3.

39. An electrodialysis apparatus for separating a first charged molecular species from a second molecular species, said apparatus comprising:
a pair of opposed electrodes including an anode and a cathode;
a retention membrane having a low molecular weight cutoff disposed between the opposed electrodes to define two cells;
a separation membrane having a high molecular weight cutoff disposed between the retention membrane and electrode in each cell to define a load channel and a dialysate channel in each of said cells, wherein the high molecular weight cutoff is at least three times the low molecular weight cutoff;
means for flowing an aqueous media containing the species to be separated to the load channels; and
means for flowing dialysate to the dialysate channels;
wherein the electrodes and load channels are disposed relative to each other so that one of the molecular species passes from the load channel through the separation membrane to the dialysate channel and the other of the molecular species remains within the load channel when electrical potential across the electrodes and differential pressure across the separation membrane are selectively controlled; and
wherein the retention membrane has a molecular weight cutoff in the range from 200 D to 200 kD and the separation membrane has a molecular weight cutoff from 600 D to 1000 kD.

40. An electrodialysis apparatus as in claim 39, wherein the retention membrane has a molecular weight cutoff below 1000 D and the separation membrane has a molecular weight cutoff above 10 kD.

41. An electrodialysis apparatus as in claim 39, wherein at least one of the retention membrane and the separation membrane is charged to selectively pass or inhibit passage of the first charged molecular species.

42. An electrodialysis apparatus as in claim 41, wherein the retention membrane(s) and separation membranes are oppositely charged.

43. An electrodialysis apparatus as in claim 42, wherein the separation membranes are cationic to selectively permit passage of anionic proteins and the retention membranes are anionic to inhibit passage of anionic proteins.

44. An electrodialysis apparatus as in claim 39, further comprising means for maintaining a differential pressure between the load channels and the dialysate channels.

45. An electrodialysis apparatus as in claim 39, further comprising electrode isolation membranes, each having a low molecular weight cutoff, disposed adjacent to each electrode.

46. An electrodialysis apparatus as in claim 45, wherein the electrode isolation membrane disposed adjacent to the cathode is cationic and the electrode isolation membrane disposed adjacent to the anode is anionic.

47. An electrodialysis apparatus as in claim 39, comprising a plurality of retention membranes disposed alternately with separation membranes, and further comprising manifold means for delivering and collecting both aqueous media and dialysate to and from the load and dialysate channels, respectively.

48. An electrodialysis apparatus as in claim 39, wherein both the first and second molecular species are proteins.

49. An electrodialysis apparatus as in claim 39, wherein a ratio of the weight of the first molecular species to the weight of the second molecular species is more than ⅓ and less than 3.

50. A method for separating a charged first molecular species from a second molecular species in an aqueous media, said method comprising:
flowing the aqueous media between a retention membrane having a low molecular weight cutoff of at least 200 D and a separation membrane having a high molecular weight cutoff, wherein the high molecular weight cutoff is at least three times the low molecular weight cutoff and the separation membrane will pass both the first and second molecular species and the retention membrane will pass neither of the molecular species;

flowing dialysate over a surface of the separation membrane opposite to the surface in contact with the aqueous media flow; and controlling electrical potential and differential pressure across the separation and retention membranes in order to selectively pass one of the molecular species through the separation membrane into the dialysate and contain the other of the molecular species between the separation and retention membranes in the aqueous media.

51. A method as in claim 50, wherein the aqueous media flows through a plurality of load channels, wherein the dialysate flows through a plurality of dialysate channels interdigitated with the load channels and separated therefrom on a first side by the separation membrane and on a second side by the retention membrane.

52. A method as in claim 50, wherein an electrical potential is maintained to pass the charged first molecular species across the separation membrane into the dialysate.

53. A method as in claim 52, wherein a pH of the aqueous media is controlled at an isoelectric point of the second species to enhance retention of the second species in the aqueous media.

54. A method as in claim 52, wherein pH of the dialysate is controlled at an isoelectric point of the first charged molecular species to neutralize the charge and enhance retention of the first species in the dialysate.

55. A method as in claim 52, wherein there is substantially no differential pressure across the separation membrane.

56. A method as in claim 52, wherein a differential pressure is maintained so that aqueous media flows through the separation membrane into the dialysate to enhance transport of the charged first molecular species and wherein the separation membrane inhibits passage of the second molecular species.

57. A method as in claim 56, wherein the second molecular species is charged oppositely to the first molecular species and wherein the separation membrane is charged to selectively pass the first molecular species and inhibit passage of the second molecular species.

58. A method as in claim 50, wherein a differential pressure is maintained so that aqueous media flows through the separation membrane and carries the second molecular species into the dialysate and wherein an electrical potential is maintained to retain the charged first molecular species against the retention membrane.

59. A method as in claim 50, wherein at least one of the molecular species is a protein.

* * * * *